(12) United States Patent
Sanders et al.

(10) Patent No.: US 6,282,943 B1
(45) Date of Patent: Sep. 4, 2001

(54) APPARATUS AND METHOD FOR DETECTING SUBSTANCES

(75) Inventors: Donald G. Sanders, Combine; Gary Stephen Jennings, Garland, both of TX (US)

(73) Assignee: Basic Resources, Inc., Dallas, TX (US)

( * ) Notice: Subject to any disclaimer, the term of this patent is extended or adjusted under 35 U.S.C. 154(b) by 0 days.

(21) Appl. No.: 09/387,081

(22) Filed: Aug. 31, 1999

(51) Int. Cl.$^7$ .................................................. G01M 19/00
(52) U.S. Cl. .......................................... 73/23.2; 73/866.5
(58) Field of Search .......................... 73/23.2, 866.5, 73/23.31, 31.05

(56) References Cited

U.S. PATENT DOCUMENTS

| | | |
|---|---|---|
| 243,741 | 7/1881 | Tudor . |
| 3,289,465 | 12/1966 | Parker .................................. 73/40.5 |
| 3,308,424 | 3/1967 | Simpkins et al. ...................... 340/16 |
| 3,658,180 * | 4/1972 | Prosser ................................ 210/96.1 |
| 3,830,480 * | 8/1974 | Grant .................................. 73/866.5 |
| 3,922,921 * | 12/1975 | Woo .................................... 73/866.5 |
| 4,013,953 * | 3/1977 | Skala ................................. 73/861.77 |
| 4,261,204 | 4/1981 | Donaldson ....................... 73/421.5 R |
| 4,571,997 * | 2/1986 | Kepple et al. ........................... 73/215 |
| 4,944,861 * | 7/1990 | Reber .................................... 204/428 |
| 5,109,718 * | 5/1992 | Gugel et al. ......................... 73/866.5 |
| 5,174,325 * | 12/1992 | Okel et al. ........................... 73/866.5 |
| 5,351,524 | 10/1994 | Lanham .......................... 73/40.5 R |
| 5,421,652 * | 6/1995 | Kast et al. .......................... 73/866.5 |
| 5,522,253 * | 6/1996 | Knight ................................ 73/23.2 |
| 5,577,895 * | 11/1996 | Franklin et al. ...................... 417/238 |
| 5,595,088 * | 1/1997 | Horner ............................... 73/290 V |
| 5,612,499 | 3/1997 | Andrew et al. ...................... 73/866.5 |
| 5,687,606 | 11/1997 | Reilly ...................................... 73/73 |
| 5,756,908 | 5/1998 | Knollmeyer et al. ............... 73/866.5 |
| 5,798,696 | 8/1998 | Wong ................................... 340/605 |
| 5,948,694 * | 9/1999 | Reber et al. ......................... 436/518 |
| 6,035,657 * | 3/2000 | Dobak, III ............................ 62/293 |
| 6,053,871 * | 4/2000 | Cockburn ............................ 600/459 |

OTHER PUBLICATIONS

Operation and Calibration Manual on Gas–Sentry® Detectors, published by Bascom–Turner Instruments of 1–34 Norwood, MA, Part No. OM–995, pp. 1–34 (no date indicated on this manual).

* cited by examiner

Primary Examiner—Hezron Williams
Assistant Examiner—Michael Cygan
(74) Attorney, Agent, or Firm—Worsham Forsythe & Wooldridge LLP

(57) ABSTRACT

An exemplary apparatus and method for detecting substances are provided for allowing any of a variety of substances, such as natural gas, to be detected from a distance. The apparatus for detecting a substance includes a pole, a probe, and an elastic tube. The pole includes a first end, a second end, a first opening, a second opening, and a passage extending in the pole from the first opening to the second opening. The probe receives the substance and couples to the second opening of the pole, and the elastic tube is positioned within the passage of the pole and extends from the second opening of the pole to the first opening. A method for making an apparatus to detect a substance is also provided.

28 Claims, 6 Drawing Sheets

APPARATUS AND METHOD FOR DETECTING SUBSTANCES

TECHNICAL FIELD OF THE INVENTION

This invention relates in general to the field of mechanical apparatuses and methods and more particularly to an apparatus and method for detecting substances, such as natural gas, from a distance.

BACKGROUND OF THE INVENTION

The accumulation of combustible gas in a dwelling or building, such as natural gas that is commonly found in a home or building, is extremely dangerous and may result in catastrophic losses of human life and property. Fortunately, this problem has been greatly reduced through the introduction of "odorized" natural gas. Odorized natural gas allows gas leaks to be detected by smell before large accumulations occur. Other situations, however, have not been solved by the introduction of odorized gas.

An especially insidious problem that still exists involves the accumulation of combustible gas within a sewer system of a home or dwelling. Sewer pipes, such as those leading up to a house, underneath a house, and within the walls of a house, often develop cracks or leaks that are undetectable. These cracks or leaks can go undetected for many years. This is because the cracks are normally out of view and often do not significantly degrade the performance of the sewer system.

Serious problems arise when a crack or leak in a sewer system is combined with a natural gas leak. Sewer systems normally include sewer vents that provide needed ventilation to the sewer system. Sewer vents normally extend to the roof of a building and are open so that sewer gasses may escape out of the sewer system. Whenever a crack or leak is present in a sewer system, the sewer vents act as a draw, like a draw from a chimney, such that gasses that reside near a crack or leak in the sewer system are swept or drawn into the sewer system through the opening of the crack or leak. Other conditions may also allow the escaping natural gas to migrate to the sewer system through its cracks and leaks. The presence of natural gas near such a crack or leak can result in catastrophic losses.

The crack or leak in the sewer system may introduce natural gas or allow natural gas to migrate throughout a house or dwelling in the various sewer pipes that run underneath and within the walls and floors. Unfortunately, because sewer systems contain traps to prevent the introduction of sewer gasses and odors within a house or building, the odorized natural gas cannot be detected within the house, even though it may actually permeate a large portion of the sewer system. An ignition source may result in substantial human loss and property loss.

The presence of natural gas in a sewer system is often detected by reports of natural gas being smelled outside of a house or building. This is often because the natural gas is being vented through the sewer vents. Because of the potential catastrophic effect of natural gas in a sewer system, gas companies often check the sewer vent of a house or building when a report of a natural gas leak is made.

Unfortunately, it is often extremely difficult and dangerous for workers to access such sewer vents on roofs. Falls from ladders and falls through rotten or deteriorated roofs are not uncommon when workers are attempting to check sewer vents for the presence of gas. On-the-job injuries are not uncommon from such activity, especially back injuries from carrying heavy ladders over a distance to access a convenient point to access a roof. The placement of ladders can also damage property, such as roof edges and landscaping, in addition to the dangers associated with detecting natural gas in a sewer system. It also take considerable time to access a roof in order to check for the presence of natural gas, resulting in fewer vents being checked.

The ability to safely and expeditiously check sewer vents for the presence of natural gas is important. Unfortunately, prior attempts to solve this significant problem have been inadequate in several respects. For example, prior attempts at using a retractable pole with an external hose and a chain mounted probe to sample the gas in the sewer vent have presented significant disadvantages. The external hose presents several problems that include the exposure of the hose to the elements which may result in holes or deterioration of the hose, which can result inaccurate readings potentially resulting in catastrophic consequences through false negative detections. The excess hose also requires more pumping power to retrieve a sample of the gas from the sewer vent, which results in an increase in the time that it takes to obtain a reading, and results in storage problems when the hose must be stored between uses.

The chain mounted probe presents the significant disadvantage and difficulty in lowering the probe into a sewer vent. This may result in false negative readings because of errors in inserting the probe in a vent. It becomes virtually impossible, unless one has a complete view, to verify that the probe has properly and sufficiently entered the vent. This also presents a considerable strain on the user's back to hold the entire pole assembly while guiding the probe into the sewer vent, and then holding the pole while waiting on a reading or detection.

SUMMARY OF THE INVENTION

From the foregoing it may be appreciated that a need has arisen for an apparatus and method for detecting substances, such as natural gas, that allow such substances to be conveniently, quickly, and safely detected from a distance. In accordance with the present invention, an apparatus and method for detecting substances are provided that substantially eliminate one or more of the disadvantages and problems outlined above.

According to one aspect of the present invention, an apparatus for detecting a substance from a distance is provided that includes a pole, a probe, and an elastic tube. The pole includes a first end, a second end, a first opening, a second opening, and a passage extending in the pole from the first opening to the second opening. The probe receives the substance to be detected and couples to the second opening of the pole. The elastic tube is positioned within the passage of the pole and extends from the second opening of the pole to the first opening.

According to another aspect of the invention, an apparatus for detecting a substance from a distance is provided that includes a pole, a probe, a probe coupling, a detector, and a detector coupling. The pole has a first end, a second end, a passage extending longitudinally in the pole that serves as a passage for the substance, a first opening to the passage, and a second opening to the passage. The probe couples to the pole at the second opening through the probe coupling and receives the substance to be detected. The detector couples to the pole at the first opening through the detector coupling, which provides a path to the passage of the pole, and detects the presence of the substance.

According to other aspects of the present invention, a method for detecting a substance, using an apparatus for detecting a substance, and a method for making an apparatus for detecting a substance are also provided.

The present invention provides a profusion of technical advantages that include the capability to easily, conveniently, and quickly setup, assemble, use, disassemble, and store an apparatus for detecting substances that saves time, reduces injuries to users and workers, reduces property damage, and performs an extremely valuable safety test.

Another technical advantage of the present invention includes the capability to accurately detect a substance without having to access the roof of a house of building. This significantly reduces the time required to perform the job and substantially eliminates on-the-job injuries due to associated falls and mishaps. Potential property damage is also significantly reduced.

Another technical advantage of the present invention includes the capability to check multiple locations or vents because of the increased time savings. This significantly improves overall safety and reduces the chances of a catastrophic event.

Yet another technical advantage of the present invention includes the capability to easily retract a telescoping pole through the use of an elastic tube that is internal to the pole. The elastic pole is provided within the telescoping pole, which protects it from the elements and reduces the chances of inaccurate readings.

Still yet another technical advantage of the present invention includes the capability for the user to rest the apparatus on the vent (sewer vent) so that the user can relax and so that longer readings may be taken to ensure more accurate readings.

Still yet another technical advantage includes the capability to mount the detector on the apparatus which allows for easier use by the user and increased convenience.

Other technical advantages are readily apparent to one skilled in the art from the following figures, description, and claims.

BRIEF DESCRIPTION OF THE DRAWINGS

For a more complete understanding of the present invention and the advantages thereof, reference is now made to the following brief description, taken in connection with the accompanying drawings and detailed description, wherein like reference numerals represent like parts, in which.

DETAILED DESCRIPTION OF THE INVENTION

It should be understood at the outset that although an exemplary implementation of the present invention is illustrated below, the present invention may be implemented using any number of techniques, whether currently known or in existence. The present invention should in no way be limited to the exemplary implementations, drawings, and techniques illustrated below, including the exemplary design and implementation illustrated and described herein.

Figure 1:
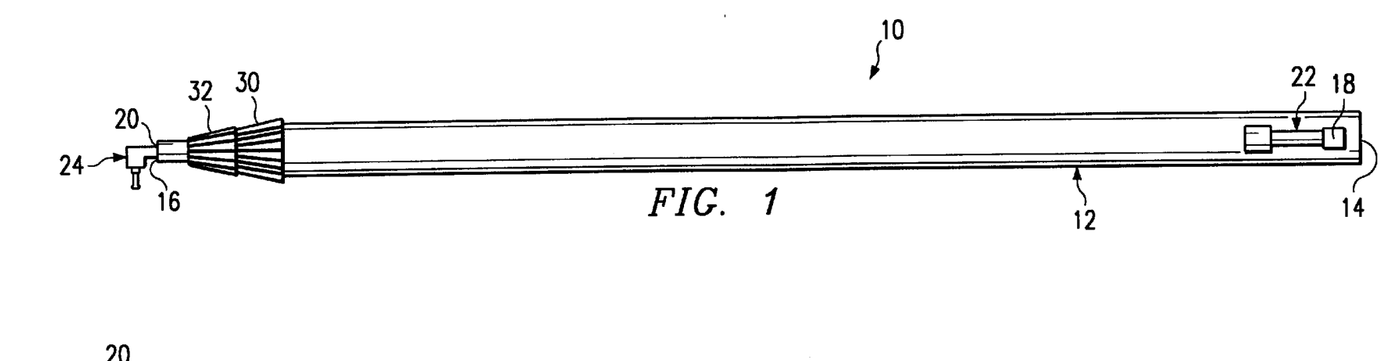
FIG. 1 is a side view that illustrates an apparatus in a retracted position that can be used for detecting a substance from a distance, according to an embodiment of the present invention.

FIG. 1 is a side view that illustrates an apparatus 10 in a retracted position that can be used for detecting a substance, such as natural gas that seeps or migrates into a sewer system of a building, according to an embodiment of the present invention. The apparatus 10 includes a retractable pole 12 with a first end 14, a second end 16, a first opening 18, and a second opening 20, along with a detector coupling 22, and a probe coupling 24. The apparatus 10 also includes an elastic tube, not shown in FIG. 1, that is positioned within a passage that resides within the retractable pole 12 and extends, in this embodiment, longitudinally within the extractable pole 12 from, preferably, the first opening 18 and the second end 16. It should also be noted that the second end 16 and the second opening 20 are provided in the same location, that is at the second end of the retractable pole 12, in the one embodiment shown in FIG. 1.

Figures 3, 4:
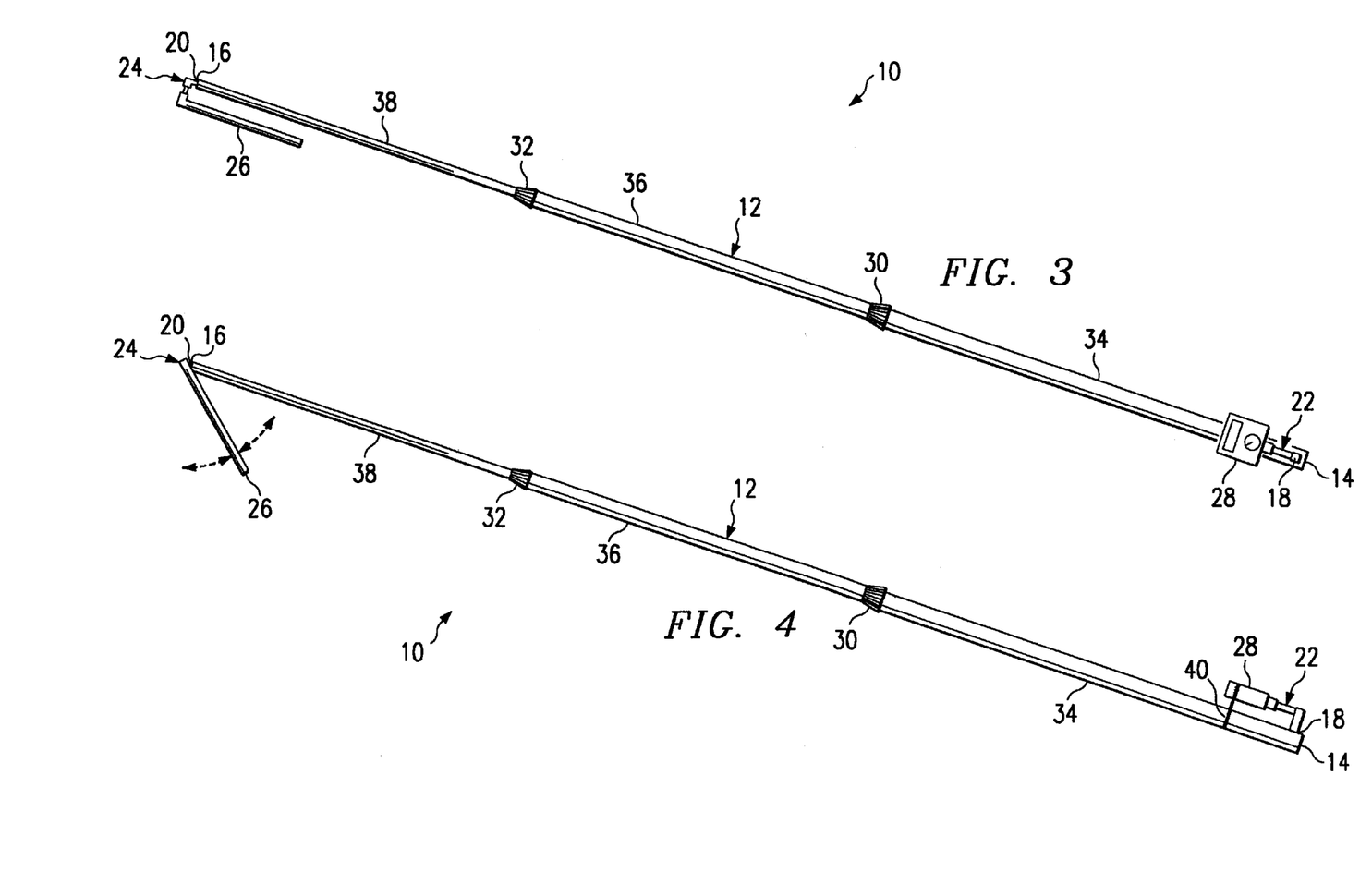
FIG. 3 is a side view that illustrates the apparatus of FIG. 2 with a detector coupled to a first opening of the retractable pole and a probe coupled to a second end of the retractable pole.
FIG. 4 is a rotated view of FIG. 3 that illustrates how the probe may move to various positions for greater versatility of use, according to one embodiment of the present invention.
Figure 5:
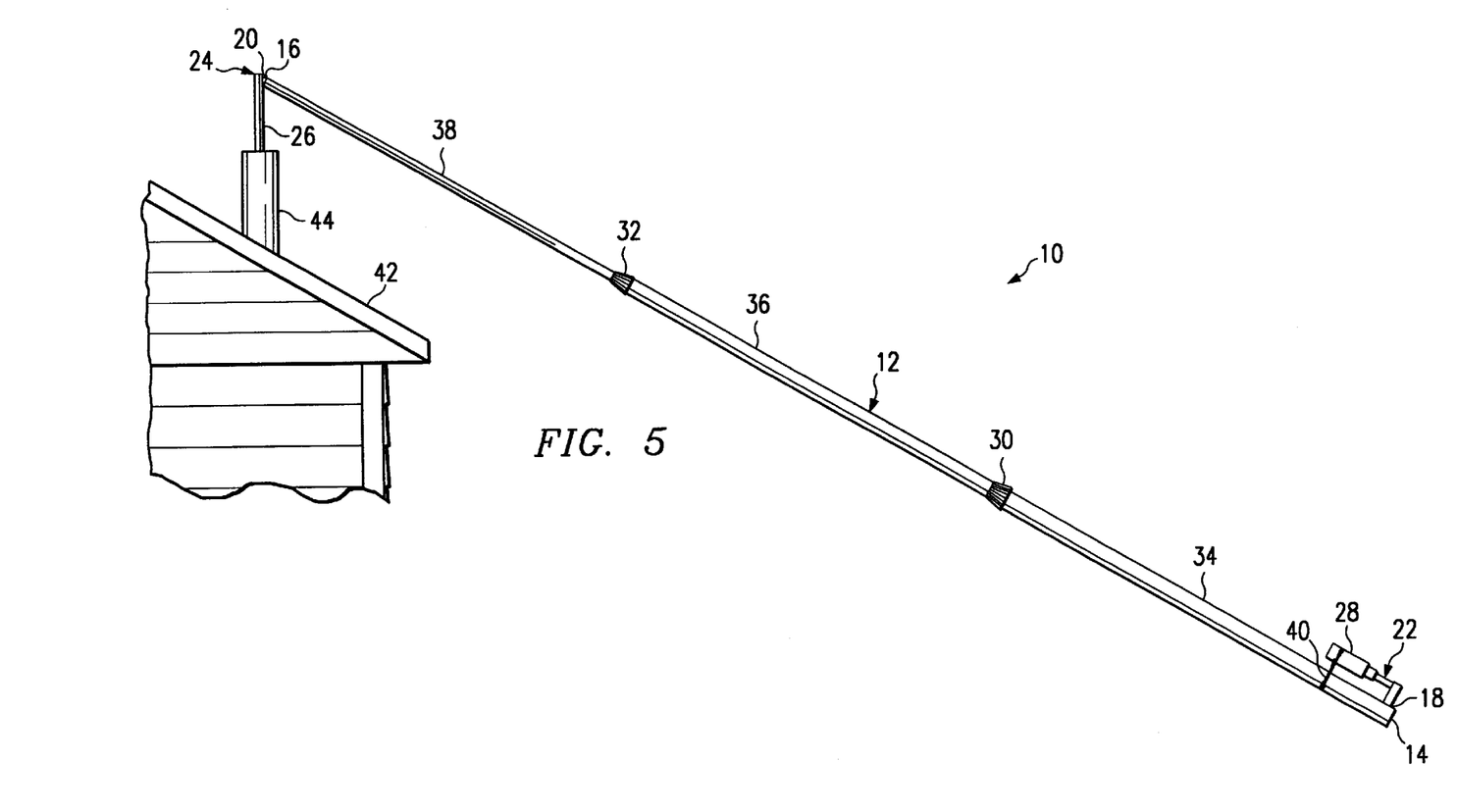
FIG. 5 is a side view that illustrates one use of the apparatus of the present invention in an environment for detecting substances at a distance, such as natural gas within a sewer vent of a building.

The apparatus 10, as will be illustrated in the FIGS. 3 through 5, will preferably include a probe 26 coupled with or in communication with the probe coupling 24, and a detector 28 coupled to or in communication with the detector coupling 22. In alternative embodiments, an auxiliary tube may couple between the detector coupling 22 and the detector 28 such that the detector may be placed on the ground, or worn on a shoulder strap or belt clip by a user of the apparatus 10.

Generally, when the apparatus 10 is to be stored, the probe 26 and the detector 28 may be conveniently removed so that the apparatus 10, as shown in FIG. 1, can be slid into a storage bin on a work truck or vehicle. For example, gas utility workers often use work trucks that include various racks for carrying ladders, tools, and equipment. It is not uncommon to see a four or six inch PVC pipe mounted on such racks so that elongated tools, such as the apparatus 10, may be conveniently stowed on the work truck or vehicle.

In a preferred embodiment, both the detector coupling 22 and the probe coupling 24 will be implemented using a quick connect/disconnect coupling so that the detector 28 and the probe 26 may be quickly and conveniently connected or disconnected from their respective coupling points. In an alternative embodiment, the detector coupling 22 may be implemented at the first end 14 of the retractable pole 12, in such a case, the first opening 18 would be positioned at the first end 14, similar to what was described above with respect to the second opening 20 being positioned at the second end 16.

A screw coupling 30 and a screw coupling 32 of the retractable pole 12 are also shown in FIG. 1. The screw couplings are typically found on retractable poles and are used to hold the various sections of the retractable pole 12 in position when they are retracted. The various segments or sections of the retractable pole 12 are illustrated more fully in FIG. 2 and may be retracted to virtually any desired length, up to their maximum length, and held into place using the screw couplings. The retractable pole 12 may also be referred to as a telescoping member or pole. In alternative embodiments, the retractable pole 12 is provided with hinge connections between each section or segment.

In operation, the apparatus 10 is removed from its storage bin and the probe 26 is coupled to the second opening 20 of the retractable pole 12 through the probe coupling 24. Similarly, the detector 28 couples to the retractable pole 12 through the detector coupling 22. A mounting strap, such as an elastic band, or other mount, neither of which are shown in FIG. 1, may be used to help secure the detector 28 relative to the retractable pole 12.

The retractable pole 12 is then extended to a desired length and the screw coupling 30 and/or the screw coupling 32 are used to fix the extended length of the retractable pole 12. An operator or user of the apparatus 10, generally positioned near the first end 14, lifts the retractable pole such that the probe 26 is placed in a desired location. For example, a user of the apparatus 10 may be checking for natural gas or methane present in the sewer system of a building or dwelling. In such a case, the user of the apparatus 10 may place the probe 26 within the sewer vent opening on the roof of the building or dwelling. A substance or gas path is established between the probe 26 and the detector 28. This path extends from the probe 26, through the probe coupling 24, the tube, which preferably will be an elastic tube that is positioned within the passage within the retractable pole 12, to the detector coupling 22, and finally to the detector 28.

In this manner, the user or worker may quickly and conveniently check for the presence of natural gas in the sewer system without having to incur the time and effort required to ascend to the roof of the building or structure. This provides substantial cost and safety savings. The safety savings include reduced risk of injury from falls or accidents by the user or worker, along with better compliance and checking of homes that may have potentially catastrophic natural gas leaks in their sewer systems.

The apparatus 10 may be made from any of a variety of materials that are known or available. For example, the retractable pole 12 will preferably be made of a nonconductive material, such as fiberglass or other nonconductive material. In an alternative embodiment, a nonconductive handle or padding will be provided at or near the first end 14 so that a user of the apparatus 10 will be electrically insulated. This is especially needed when the retractable pole 12 is made of a conductive material, such as aluminum or other metal. The operation of the apparatus 10 can be especially dangerous when overhead electrical power lines are present. The use of retractable pole 12 could result in the pole coming in contact with such overhead electrical power lines. As such, it is not advisable to use the retractable pole 12 near overhead power lines.

In an alternative embodiment, an elastic tubing may not be positioned within the passage that extends longitudinally within the retractable pole 12. In such a case, the longitudinal passage within the retractable pole 12 serves as the conduit or path to connect the probe 26 to the detector 28 so that any gases or substances present at the probe 26 may be received and analyzed by the detector 28. In such a case, "O" rings or other parts and materials may be used to provide a full or partial seal between the various segments or sections of the retractable pole 12. In this manner, the longitudinal passage within the retractable pole 12 allows substances such as gases to be received at the probe 26 and provided to the detector 28. This is discussed more fully in connection with FIG. 6.

The detector coupling 22 and the probe coupling 24 may be made of virtually any available material such as brass or copper couplings that are commonly used in plumbing and other household applications.

Figure 2:
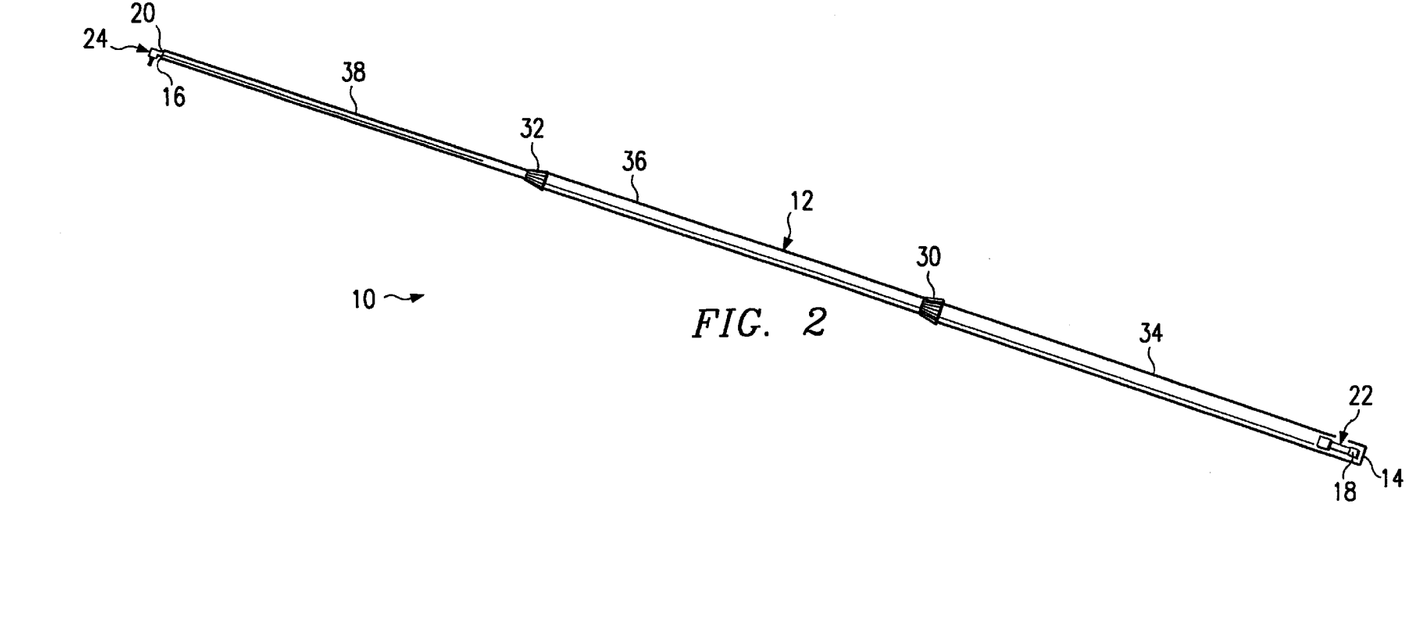
FIG. 2 is a side view that illustrates the apparatus of FIG. 1 in an extended position.

FIG. 2 is a side view that illustrates the apparatus 10 of FIG. 1 in an extended position. The retractable pole 12 includes three sections that are blocked or secured relative to one another through the screw coupling 30 and the screw coupling 32. In a preferred embodiment, an elastic tubing, not shown in FIG. 2, positioned within the longitudinal passage of the retractable pole 12 extends between the probe coupling 24 and the detector coupling 22 to provide a path for substances to be received at the probe 26 and provided to the detector 28. When the retractable pole 12 is converted from the extended position shown in FIG. 2 to the retracted position shown in FIG. 1, the mechanical force from the stretched elastic tubing assists with the closing or retraction of the retractable pole 12. This significantly assists with retracting the retractable pole 12.

In an alternative embodiment, the longitudinal passage within the retractable pole 12 serves as the path for substances or gases to be provided from the probe 26 to the detector 28. In the embodiment shown in FIG. 2, the retractable pole 12 includes three circular shaped segments, which include a first segment 34, a second segment 36, and a third segment 38. As is illustrated, the first segment 34 has a larger diameter than the second segment 36. Similarly, the second segment 36 has a larger diameter than the third segment 38. This results in an internal passage within the first segment 34 that is larger than the internal passage in the second segment 36. Similarly, the internal passage or hollow area within the second segment 36 is larger than the third segment 38. As can be seen, the second segment 36 may be stored within the first segment 34, and the third segment 38 may be stored within both the second segment 36 and the first segment 34. This is more fully illustrated in FIG. 6.

FIG. 3 is a side view that illustrates the apparatus 10 of FIG. 2 with the detector 28 coupled to the first opening 18 through the detector coupling 22 of the retractable pole 12. The probe 26 is also shown coupled to the second end 16 and the second opening 20 of the retractable pole 12 through the probe coupling 24. As discussed above, the probe coupling 24 and the detector coupling 28 are preferably provided as quick connect/disconnect coupling such that the probe 26 and the detector 28 may be conveniently and quickly connected and disconnected as desired.

In alternative embodiments, the second opening 20 may be provided at a position other than the second end 16 of the retractable pole 12. In such a case, the probe coupling 24 may be mounted or positioned at the second opening 20 to provide a conduit or connection between the probe 26 and the elastic tubing or internal longitudinal passage of the retractable pole 12.

The detector 28 may be mounted directly or in close proximity to the retractable pole 12, as illustrated in FIG. 3. In alternative embodiments, the detector 28 may be worn on a user's belt or on a user's shoulder through a shoulder strap and an auxiliary tube may be used to couple the detector to the apparatus 10 through the detector coupling 22.

The detector 28 will generally be a gas detector that can detect the presence of one or more gases. For example, the detector 28 may detect the presence of natural gas, methane, propane, ethane, butane, carbon monoxide, helium, hydrogen sulfide, oxygen, freon, or any other gas, such as a combustible or potentially harmful gas. In a preferred embodiment, the detector 28 is a battery powered detector that includes a pump that allows the gases that are received at the probe 26 to be pulled or sucked through the probe 26 and through the path that is defined through the probe coupling 26, the elastic tubing, the detector coupling 22 and received at the detector 28. This eliminates the need to have a separate pump or a manual pump or aspirator bulb which can significantly increase the time that it takes to get an accurate reading and may result in inaccurate readings due to insufficient pumping. This also reduces the overall time that is needed to obtain an accurate reading. The detector 28 may be similar to one that is manufactured by Bascom-Turner Instruments, such as the Gas-Sentry and the Gas-Ranger detectors and analyzers. These detectors generally include an automatic calibration feature and a built-in, battery-powered pump.

The probe 26 may be made of virtually any available material, such as copper, brass, and even certain plastics or polymers. The probe 26 will generally include a center passage that allows for substances, such as gases, to be passed through a longitudinal passage in the probe 26.

The advantage of using an internal elastic tube, or in the alternative embodiment where there is no elastic tubing but instead the longitudinal passage is used within the retractable pole 12, are substantial. An external tube or hose is cumbersome to work with, is exposed to the elements, is susceptible to leaks and deterioration, is inconvenient to store, and generally can hamper the overall operation of the apparatus 10.

FIG. 4 is a rotated view of FIG. 3 that illustrates how the probe 10 may move to various positions for greater versatility of use, according to one embodiment of the present invention. The apparatus 10 that is illustrated in FIG. 4 is the same as that illustrated in FIG. 3 except that the retractable pole 12 has been rotated 90 degrees clockwise. This presents a side view of the detector 28 and illustrates the use of an optional strap 40 (also referred to as a mount 40), that may be used to help secure the detector 28 relative to the retractable pole 12.

The probe 26 is also shown having a rotational coupling with the probe coupling 24. This provides significant advantages and allows for the apparatus 10 to be used on roofs of varying or different slopes or inclines and to be used in vents or other gas sample locations that are provided at different angles. This is illustrated more fully in FIG. 5. One way to visualize the potential rotational positions of the probe 26 relative to the second end 16 of the retractable pole 12 is to think of the probe as a fan or propellor blade that, in one embodiment, may rotate 360 degrees relative to the second end 16 of the retractable pole 12.

In alternative embodiments, the detector 28 may be positioned at or near the second end 16, such that the detector 28 may produce some type of signal, such as an audible, visible, remote, or wireless signal, when one or more gasses or substances are detected. In such a case, the first opening 18 will be provided nearer to the second end 16, and the longitudinal passage in the retractable pole 12 will be much shorter and may only span a short distance and may not extend longitudinally.

FIG. 5 is a side view that illustrates one use of the apparatus 10 of the present invention in an environment for detecting substances, such as gases, at a distance. For example and for the reasons explained previously, it is often desirable to check for the presence of natural gas, such as methane, within a sewer vent of a building or structure. A structure 42, such as a building or dwelling, is shown with a vent 44, such as a sewer vent, in FIG. 5. A user of the apparatus 10 may extend the retractable pole 12 and position the probe 26 within the vent 44. The probe 26 may then be slid within the opening of the vent 44 to obtain a sample of the gases within the vent 44. The probe 26 is not shown fully positioned within the vent 44. Once the probe 26 is positioned within the vent 44, a user may place the apparatus 10 down without having to continuously support the apparatus 10. This provides significant advantages to workers and significantly reduces injuries. This further allows the probe 26 to be provided within the vent 44 for an adequate time to obtain suitable gas samples.

The detector 28, which preferably includes a pump, will suck or pump the gas sample from within the vent 44 through the probe 26 and through the path previously described until it arrives at the detector 28, where it can be properly analyzed.

Figure 6:
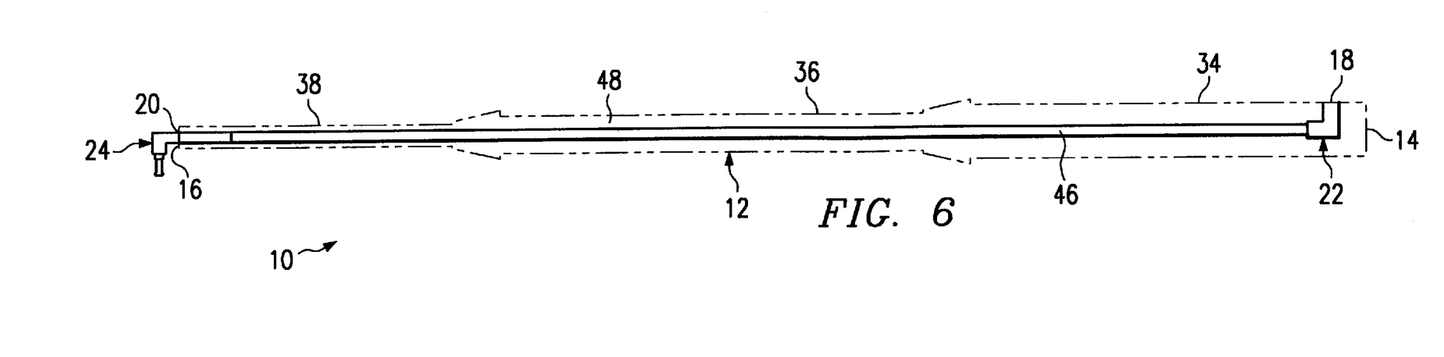
FIG. 6 is a side, internal view of the apparatus that illustrates an internal tube that extends along an longitudinal passage of the retractable pole.

FIG. 6 is a side, internal view of the apparatus 12 that illustrates an elastic tube 46 positioned within a longitudinal passage 48 of the retractable pole 12. As is illustrated, the elastic tube is shown extended between the detector coupling 22 and the probe coupling 24. In one embodiment, the elastic tube 46 is implemented using surgical tubing and is coupled to the respective couplings through the combination of a friction fit and an external fastener to bind or tie the elastic tube 46 to the coupling. In this manner, the elastic tube 46 resides within the longitudinal passage 48 and provides a pathway from the first opening 18 to the second opening 20 while the apparatus 10 is in a retracted position, an extended position, or some position in between.

Figure 7:
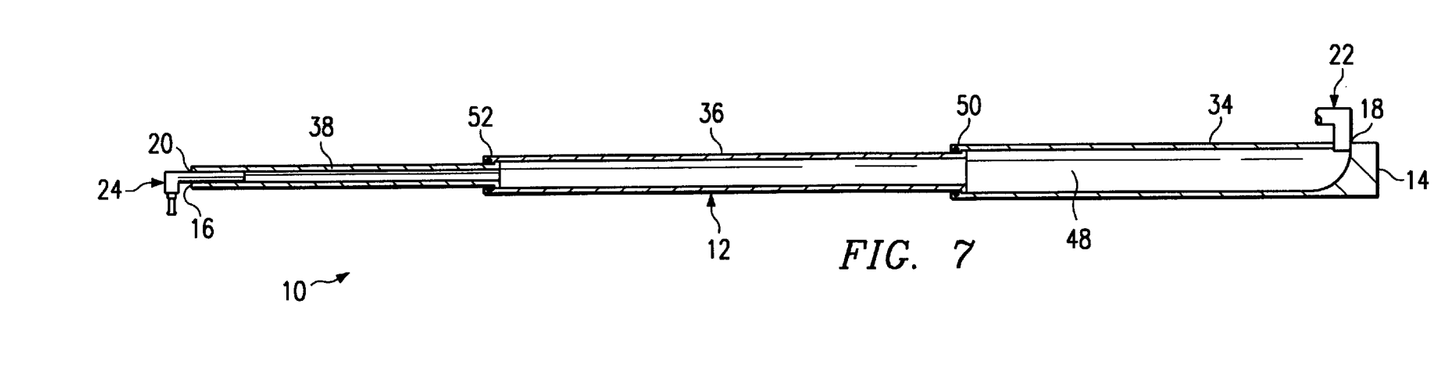
FIG. 7 is a side, internal view of the apparatus that illustrates an alternative embodiment of the present invention that includes a longitudinal passage in the retractable pole that decreases in cross-sectional area for each succeeding section from the first opening of the retractable pole to the second opening of the retractable pole.

FIG. 7 is a side, internal view of the apparatus 10 that illustrates an alternative embodiment of the present invention that includes a retractable pole 12 that includes a longitudinal passage 48 in the retractable pole 12 that decreases in cross-sectional area for each succeeding section from the first opening 18 to the second opening 20. This eliminates the need for the elastic tubing 46, which was illustrated in FIG. 6. A sealed or semi-sealed coupling will, preferably, be provided where each section of the retractable pole 12 couples with an adjoining section. For example, an "O" ring 50 may be provided between the first segment 34 and the second segment 36. The screw coupling 30, which was illustrated in FIGS. 1 through 5, may be provided over the coupling where the "O" ring 50 is provided. Similarly, an "O" ring 52 may be provided between or at the coupling of the second segment 36 and the third segment 38.

As can be seen, a passage is provided for a gas or other substance to be provided from a probe to a detector through a passage defined through the probe coupling 24, which is positioned at the second opening 20, the third section 38, the second section 36, the first section 34, the first opening 18, and the detector coupling 22. The design of the various segments of the retractable pole 12 allow for each segment to be in a telescopic relationship with the other segments.

Preferably, the volume of air that must be pumped through the passage, defined above, should be minimized. This saves on the battery life of the pump and reduces the pumping requirements from the detector or from an external pump, which is necessary to move a gas or other substance through the passage defined above.

The design shown in FIG. 7 also may be implemented using a plastic or polymer material that is lightweight. This may allow additional sections to be included in the retractable pole 12 because of the decreased weight. A plastic or lightweight probe could be used to further lighten the weight at the second end 16 of the retractable pole 12, which would provide the added benefit of allowing a longer retractable pole 12 to be used.

Figure 8:
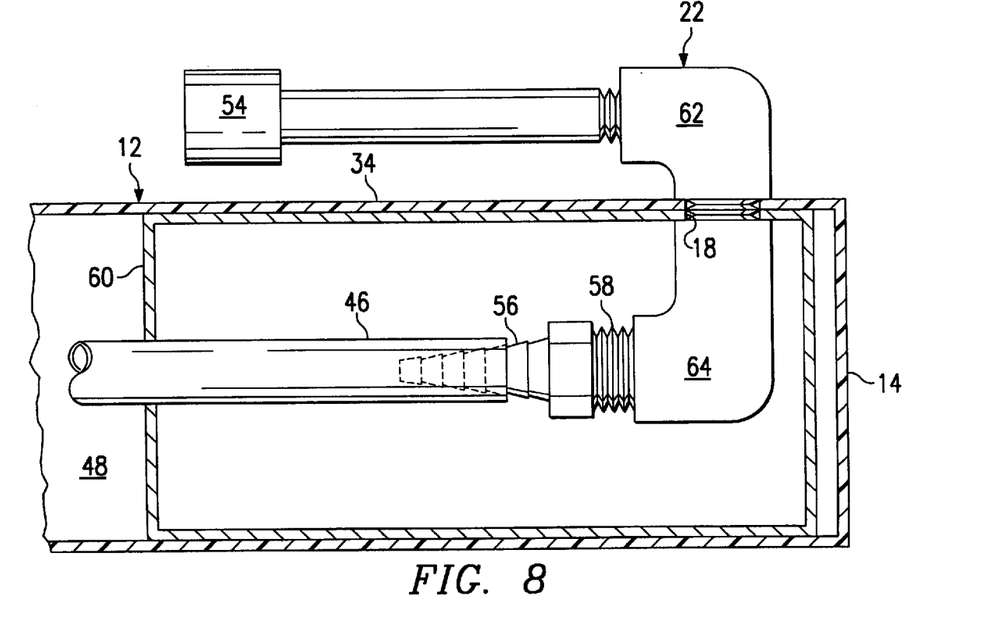
FIG. 8 is a partial, side, cutaway view that illustrates the position of the detector coupling in the first opening of the retractable pole, in the embodiment of the present invention illustrated in FIGS. 1 through 6.

FIG. 8 is a partial, side, cutaway view that illustrates the position of the detector coupling 22 in the first opening 18 of the retractable pole 12, according to an embodiment of the present invention illustrated in FIGS. 1 through 6. A sleeve 60, such as a rigid or aluminum cylindrical sleeve as shown, may be provided to provide additional mechanical rigidity and stability. This is especially useful when the retractable pole 12 is made of a plastic, polymer, or fiberglass composition that can easily crack. The sleeve 60 allows the various components or parts of the detector coupling 22 to mount or position more securely within the first opening 18.

The implementation of the detector coupling 22 of FIG. 8 includes a female quick connect coupling 54 that includes threads to couple with one end of an "L" coupling 62. The detector 28 will preferably include a corresponding male quick connect coupling that allows the detector 28 to be conveniently and quickly connected and disconnected with the female quick connect coupling 54. The other end of the "L" coupling 62 couples or interfaces with an "L" coupling 64 at an opening formed in the sleeve 60 that is near the first opening 18. The other end of the "L" coupling 64 includes a male coupling 56 that is threadably engaged therein. The male coupling 56 may also include an indent 58 so that the elastic tubing 46 may more securely interface with the male coupling 56 and may be secured by an external wrap (such as a plastic tie) or coupling around the indent 58. This further secures this coupling. In other embodiments, the plastic tie may be placed anywhere on the coupling.

In still other embodiments, the "L" coupling 62 may be implemented as a "T" coupling 62. This will provide a second coupling, opposite of the coupling shown in FIG. 8, for the detector to provide additional access to the gas or substance that is being detected. In one example, a sample of the gas or substance could be accessed at the "T" coupling and taken to a lab for further analysis. This provides the significant advantage of allowing a sample of vent or flue gas to be taken at a distance. This, in many cases, would prevent the need to access the roof of a house or dwelling.

Figure 9:
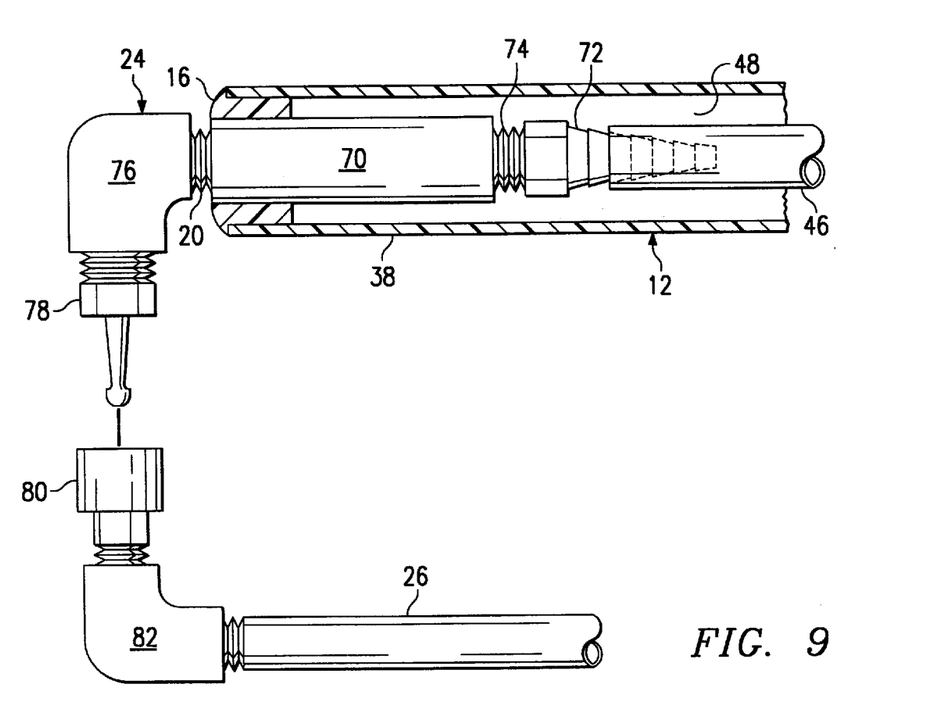
FIG. 9 is a partial, side, cutaway view that illustrates the position of the probe coupling in the second opening of the retractable pole, in the embodiment of the present invention illustrated in FIGS. 1 through 6.

FIG. 9 is a partial, side, cutaway view that illustrates the position of the probe coupling 24 in the second opening 20 of the retractable pole 12 in an embodiment of the present invention illustrated in FIGS. 1 through 6. The probe coupling 24, in the embodiment illustrated, may include a threaded coupling 70 that couples with a male coupling 72. The threaded coupling between these two components may provide an indent 74. The indent 74 provides all of the advantages and features described above in connection with the indent 58 of FIG. 8. Generally, the combination of the male coupling 72 and the indent 74 provide a convenient and secure means of coupling with the plastic tube 46.

The threaded coupling 70 of the probe coupling 24 extends through the first opening 20 where it interfaces or threadably engages an "L" coupling 76. The other end of the "L" coupling 76 threadably engages a male quick connect coupling 78. This allows the probe coupling 24 to conveniently and quickly couple with the probe 26 through a female quick connect coupling 80. In the embodiment illustrated in FIG. 9, the probe 26 includes an "L" coupling 82 that provides a coupling between the probe 26 and the female quick connect 80. In this manner, not only can the probe 26 conveniently and quickly couple with the probe coupling 24, but the significant additional advantage is provided by allowing the probe 26 to rotate in an arc or circular fashion through the quick connect coupling of the male quick connect coupling 78 and the female quick connect coupling 80. This was illustrated more fully in connection with the description accompanying FIG. 4. This provides a significant advantage of allowing the present invention to be used on roofs or vents of varying angles and dimensions.

Figure 10:
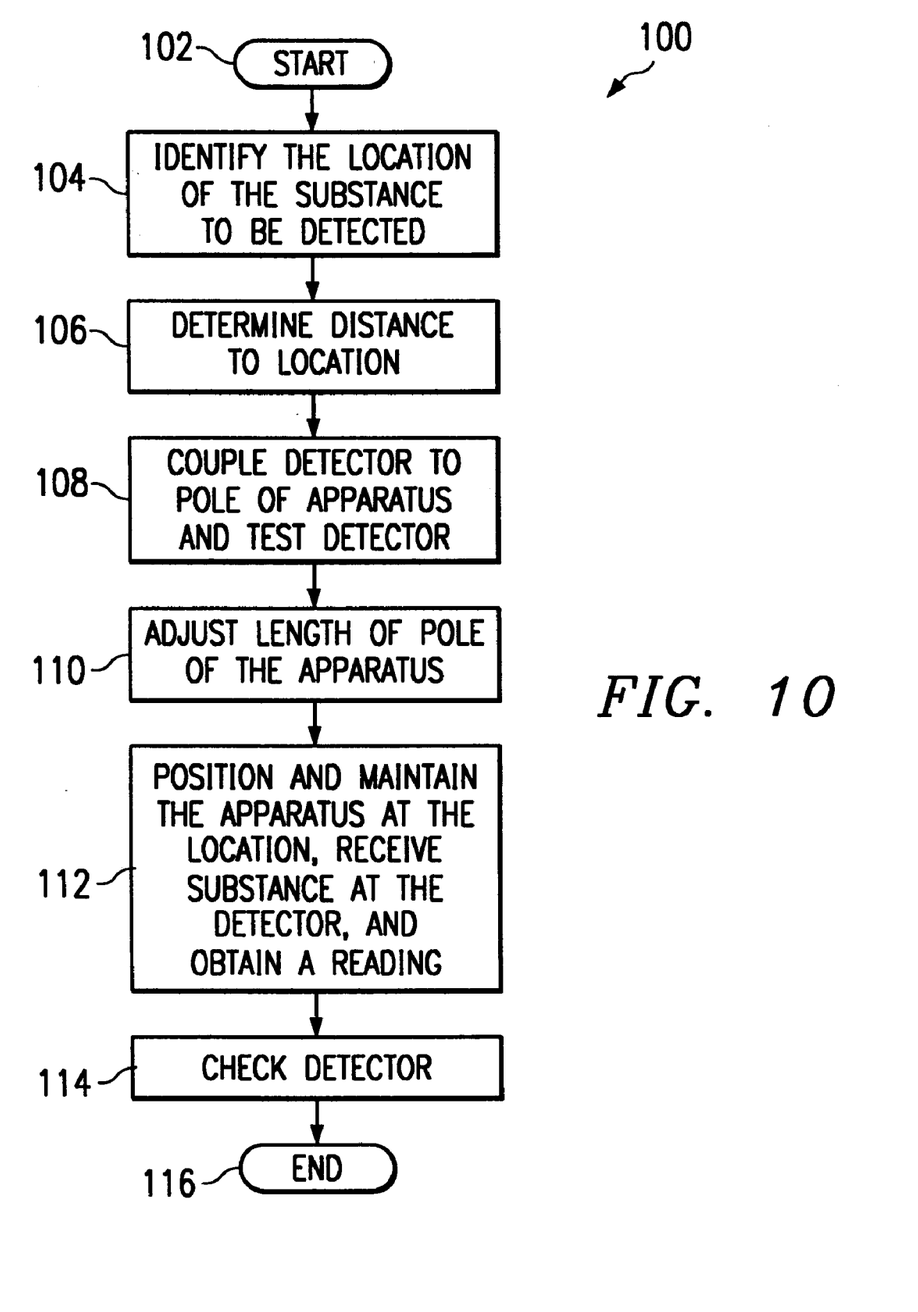
FIG. 10 is a flowchart that illustrates a method for detecting a substance, according to one embodiment of the present invention.

FIG. 10 is a flow chart of a method 100 for detecting a substance using an apparatus for detecting a substance, according to an embodiment of the present invention. The method 100 starts at block 102 and proceeds to block 104. At block 104, the location of the substance to be detected is identified. This may be, for example, locating the sewer vent on the roof of a house or a building. When locating a sewer vent, it is preferable to locate and identify the main sewer vent on the roof. The main sewer vent will generally be the largest sewer vent pipe on the roof.

The method 100 proceeds next to block 106 where the distance to the location of the substance is estimated or determined. For safety considerations, the presence of overhead obstructions, such as overhead power lines, should be closely scrutinized. Next, the method 100 proceeds to block 108 where a detector is coupled to the pole of the apparatus. The detector may then be turned on and tested. For example, the detector may be checked for lockup by placing a finger over the end of a probe of the apparatus to ensure that the detector indicates that a block has occurred.

At block 110, the length of the pole of the apparatus is adjusted to an appropriate length so that the desired location of the substance can be conveniently reached. This may involve extending various sections of the pole of the apparatus at block 110. At block 112, the apparatus should be positioned and maintained at the desired location of the substance for an appropriate period of time to get an accurate reading or detection. For example, one minute is often sufficient. This also provides sufficient time to allow a sample of the substance to be received at the detector of the apparatus to be analyzed. As mentioned previously, the detector will often include a pump that automatically pumps the sample from the probe through a passage in the pole or through an elastic tube until it is received at the detector.

After a reading has been obtained, the method 100 proceeds next to block 114 where the detector may be tested again. For example, the probe may be removed from the apparatus and the lockup of the detector can be checked again. If the test indicates that the detector is functioning correctly, the detection is complete. The method 100 then proceeds to block 116 where the method ends.

If gas or some other combustible or dangerous substance was detected by method 100, various other surrounding locations may also be checked for the presence of the same substance. For example, if natural gas is found in the sewer vent of a house or building, the surrounding structures should also be checked to determine if the substance is also found at the surrounding locations.

Thus, it is apparent that there has been provided, in accordance with the present invention, an apparatus and method for detecting substances from a distance that satisfies one or more of the advantages set forth above. Although the preferred embodiment has been described in detail, it should be understood that various changes, substitutions, and alterations can be made herein without departing from the scope of the present invention, even if all of the advantages identified above are not present. For example, the probe may be coupled at or near an end of the pole through virtually any known or available mechanisms or through one or more intermediate devices or appliances. The present invention may be implemented using any of a variety of materials and configurations. For example, the pole will, preferably, be made of a nonconductive material, but may be made of aluminum or virtually any other available material. The pole will also, preferably, be retractable and telescoping using any number of segments or pieces, but may also be implemented using a retractable arrangement that is not telescoping, but is provided in a hinged arrangement using multiple segments. These are only a few of the examples of other arrangements or configurations of the apparatus that is contemplated and covered by the present invention.

The various components, members, elements, and methods described and illustrated in the preferred embodiment as discrete or separate may be combined or integrated with other components, members, elements, and methods without departing from the scope of the present invention. The present invention may be used to detect virtually any substance that can be detected. Other examples of changes, substitutions, and alterations are readily ascertainable by one skilled in the art and could be made without departing from the spirit and scope of the present invention.

What is claimed is:

1. An apparatus for detecting a substance from a distance comprising:
    a retractable pole having a first end, a second end, a first opening, a second opening, and a passage extending in the retractable pole from the first opening to the second opening, the retractable pole operable to be placed in a retracted position and an extended position, wherein the retractable pole may be extended at least two times its length when the retractable pole is moved from the retracted position to the extended position;
    an extendable elastic tube positioned within the passage of the retractable pole and operable to provide a path from the second opening of the retractable pole to the first opening, wherein the extendable elastic tube may be extended at least two times its length when the retractable pole is moved from the retracted position to the extended position;
    a detector coupling operable to couple with a detector and to provide a path to the extendable elastic tube through the first opening of the retractable pole; and
    a probe operable to receive the substance and to provide a path to the extendable elastic tube through the second opening of the retractable pole.
2. The apparatus of claim 1, wherein the first opening of the retractable pole is positioned near the first end of the retractable pole.
3. The apparatus of claim 1, wherein the first opening of the retractable pole is positioned at the first end of the retractable pole.
4. The apparatus of claim 1, wherein the second opening of the retractable pole is positioned near the second end of the retractable pole.
5. The apparatus of claim 1, wherein the second opening of the retractable pole is positioned at the second end of the retractable pole.
6. The apparatus of claim 1, further comprising:
    a sleeve positioned within the passage of the retractable pole, the sleeve operable to couple the detector coupling to the retractable pole through the first opening.
7. The apparatus of claim 6, further comprising:
    a detector operable to couple to the detector coupling and to detect the presence of the substance.
8. The apparatus of claim 7, wherein the detector is operable to receive the substance through a path defined by a passage in the probe, the extendable elastic tube, and the detector coupling.
9. The apparatus of claim 8, wherein the detector is fixed relative to the retractable pole.
10. The apparatus of claim 9, further comprising:
    a mount operable to support the detector in relation to the retractable pole.
11. The apparatus of claim 7, further comprising:
    an auxiliary tube operable to couple between the detector and the detector coupling such that the detector couples to the detector coupling through the auxiliary tube, and wherein the detector is operable to receive the substance through a path defined by a passage in the probe, the extendable elastic tube, the detector coupling, and the auxiliary tube.
12. The apparatus of claim 8, wherein the detector is a gas detector.
13. The apparatus of claim 12, wherein the substance is a gas selected from the group consisting of natural gas, methane, propane, carbon monoxide, hydrogen sulfide, ethane, butane, oxygen, and freon.
14. The apparatus of claim 12, wherein the substance is a combustible gas.
15. The apparatus of claim 1, further comprising:
    a probe coupling positioned at the second opening of the retractable pole and operable to couple with the probe to provide a path to the elastic tubing.
16. The apparatus of claim 1, wherein the probe couples to the second opening of the retractable pole through a quick connect coupling.
17. The apparatus of claim 1, wherein the probe couples to the second opening of the retractable pole through a coupling operable to allow the probe to rotate.
18. The apparatus of claim 1, wherein the probe couples to the second opening of the retractable pole through a releasable, spring-loaded coupling.
19. The apparatus of claim 6, wherein the detector coupling is a quick connect coupling.
20. The apparatus of claim 6, wherein the detector coupling is a releasable, spring-loaded coupling.
21. The apparatus of claim 6, wherein the retractable pole is an antenna pole.
22. The apparatus of claim 1, wherein the retractable pole is a telescoping pole.
23. The apparatus of claim 22, wherein the telescoping pole has three sections.
24. The apparatus of claim 1, wherein the extendable elastic tube is surgical tubing.
25. The apparatus of claim 1, wherein the extendable elastic tube is tubing that is resistant to corrosion by the substance being detected.
26. The apparatus of claim 1, wherein the passage of the retractable pole extends generally from the first end to the second end.

27. The apparatus of claim 1, further comprising a nonconductive handle positioned on the retractable pole.

28. A method for making an apparatus for detecting a substance at a distance comprising:

providing a retractable pole having a first end, a second end, a first opening, a second opening, and a passage extending in the retractable pole from the first opening to the second opening, the retractable pole operable to be placed in a retracted position and an extended position, wherein the retractable pole may be extended at least two times its length when the retractable pole is moved from the retracted position to the extended position;

positioning an extendable elastic tube within the passage of the retractable pole to provide a path from the second opening of the retractable pole to the first opening, wherein the extendable elastic tube may be extended at least two times its length when the retractable pole is moved from the retracted position to the extended position;

providing a detector coupling operable to couple with a detector and to provide a path to the extendable elastic tube through the first opening of the retractable pole; and providing a probe operable to receive the substance and to provide a path to the extendable elastic tube through the second opening of the retractable pole.

* * * * *